United States Patent [19]

Busch-Vishniac et al.

[11] Patent Number: 4,598,590
[45] Date of Patent: Jul. 8, 1986

[54] ELECTRET TRANSDUCER FOR BLOOD PRESSURE MEASUREMENT

[75] Inventors: Ilene J. Busch-Vishniac, Austin, Tex.; Robert A. Kubli, Whitehouse Station; James E. West, Plainfield, both of N.J.

[73] Assignee: AT&T Bell Laboratories, Murray Hill, N.J.

[21] Appl. No.: 651,043

[22] Filed: Sep. 14, 1984

[51] Int. Cl.⁴ .............................................. G01L 9/12
[52] U.S. Cl. ........................................ 73/724; 73/729; 361/283
[58] Field of Search ................... 73/724, 729; 361/283; 128/680

[56] References Cited

U.S. PATENT DOCUMENTS 3,118,979  1/1964  Sessler et al. ...................... 361/283

OTHER PUBLICATIONS

J. E. West and I. J. Busch-Vishniac, "Foil Electret Transducer for Blood Pressure Monitoring," *J. Acoust. Soc. Am.*, 74(3), 680–686 (Sep. 1983).

Primary Examiner—Donald O. Woodiel
Attorney, Agent, or Firm—Jack S. Cubert

[57] ABSTRACT

A back electrode has a plurality of ridges on one surface. An electret foil is spaced from the ridged surface of the back electrode. In the absence of applied pressure, a gap remains between the foil and the surface of the back electrode between the ridges. Above one applied pressure, the foil collapses between the ridges. Below a second applied pressure, the foil returns to its original position.

11 Claims, 3 Drawing Figures

ELECTRET TRANSDUCER FOR BLOOD PRESSURE MEASUREMENT

The invention relates to pressure transducers, and in particular to electret transducers for sphymomanometry.

BACKGROUND OF THE INVENTION

A common technique for indirect blood pressure measurement depends on an occlusive cuff and a stethoscope for ausculation of Korotkov sounds. While satisfactory for many clinical purposes, the technique is subject to errors due to such factors as stethoscope efficiency, the hearing acuity of the examiner, ambient noise, and the variability in Korotkov sound intensity and spectrum between individuals. In addition, a stethoscope may be inconvenient for extended or ambulatory blood pressure monitoring.

The stethoscope may be replaced with an electrical transducer such as a microphone, piezoelectric sensor or strain gauge. A typical piezoelectric sensor consists of a small piece of piezo-ceramic material, such as lead-zirconate-titanate (PZT), cemented to the center of a larger circular metal plate. The sensitivity of this transducer is dependent on the excitation point of the metal plate. Maximum output is realized if the plate is excited at the center, but the output decreases sharply as the excitation point is shifted outward toward the edge of the plate.

Due to non-uniform sensitivity, the piezoelectric sensor must be positioned accurately over the brachial artery. If the sensor is shifted even a small amount (a not unlikely occurrence under ordinary conditions of use), the output may drop or cease entirely. The problem is aggravated for patients with obese or flabby arms, ambulatory monitoring, and patients with a weak brachial pulse. Strain gauge and microphone transducers may have similar limitations.

It is thus an object of the invention to provide a blood pressure transducer which is more accurate under a variety of clinical conditions.

SUMMARY OF THE INVENTION

The invention is directed to an improved electret transducer arrangement for blood pressure measurement. The transducer includes a back electrode having spaced ridges on one surface. An electret foil is disposed adjacent and parallel to the ridged surface of the back electrode. In the absence of applied pressure, the foil is in a first position to maintain an air gap between the back electrode and the foil. Above a first predetermined applied pressure, the foil collapses to contact the back electrode surface between the ridges. The spacing of the ridges is selected so that the foil returns to the first position responsive to reduction of the applied pressure below a second predetermined amount.

DETAILED DESCRIPTION

Figure 1:
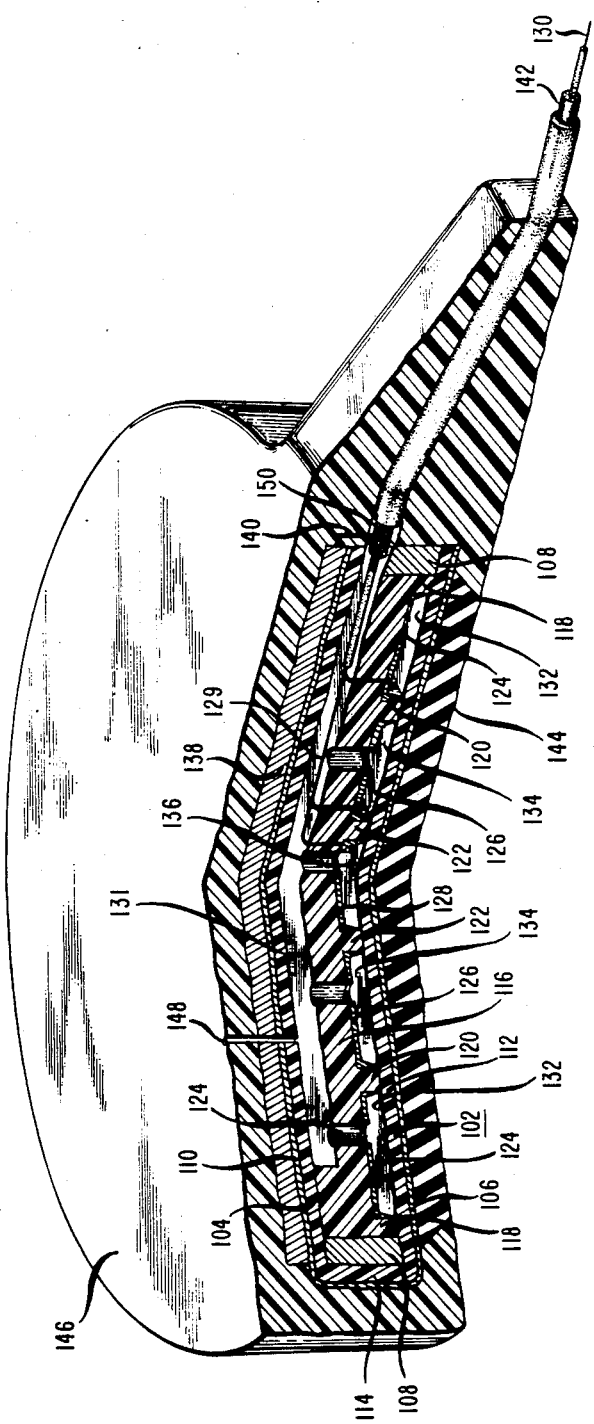
FIG. 1 shows a cross-sectional view of a transducer in accordance with the invention.

Referring to FIG. 1, transducer 100 comprises a charged electret foil 102 having a non-metalized layer 104, and a metalized layer 106. Metalized layer 106 may be, for example, aluminum. Non-metalized layer 104 may be a polymer material, such as Teflon TM FEP, polarized in the direction of its thickness. In a preferred embodiment, layer 104 is a Kapton TM -FEP composite, wherein metalizd layer 106 covers the Kapton side. Kapton provides mechanical strength and FEP provides charge storage. Kapton and Teflon FEP are trademarks of products made by E. I. Dupont De Nemours, Inc., Wilmington, Del.

Figure 2:
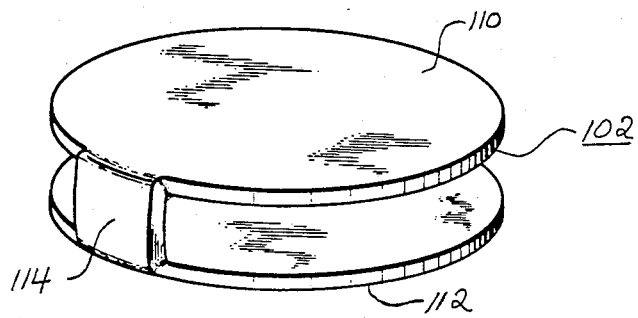
FIG. 2 shows an exploded view of an electret foil.

Foil 102 includes top and bottom portions 110 and 112 in contact with the top and bottom edges of a metal tensioning ring 108. Top and bottom portions 110 and 112 are connected by a side portion 114. As shown in FIG. 2, top and bottom portions 110 and 112 of foil 102 are circular, corresponding to ring 108, and side portion 114 is a narrow strip.

As shown in FIG. 1, a back electrode 116 is disposed inside ring 108. The bottom surface of back electrode 116 has ridges 118, 120 and 122 in spaced, concentric relationship. The areas between the ridges comprise electrically conductive valleys 124, 126 and 128. For illustrative clarity, the height of the ridges above the valleys has been exaggerated; in reality the ridge heights are comparable to the height of features on a coin.

In the preferred embodiment shown in FIG. 1, the body of back electrode 116 is an insulative plastic or epoxy material and conductive valleys 124, 126 and 128 comprise an evaporatively deposited metal, such as aluminum. Alternatively, the entire back electrode may be made of an electrically conductive material, in which case it would be desirable to electrically isolate the electrode from foil 102. Valleys 124, 126 and 128 are electrically interconnected, for example via conductor 129, to output 130.

A back cavity 131 is defined by back electrode 116 and the top portion 110 of foil 102. Air gaps 132, 134 and 136 are defined by valleys 124, 126 and 128, and the bottom portion 112 of foil 102. A plurality of holes 124 connect air gaps 132, 134 and 136 with back cavity 131.

A metal back cover 138 is disposed in contact with the metalized layer 106 of top portion 110 of foil 102. Back cover 138 is electrically connected via conductor 140 to ground 142. The entire metalized layer 106 of foil 102 is therefore connected to ground. Ring 108 is also connected, at point 150, to ground 142. Advantageously, the top and bottom portions 110 and 112, and ring 108 thereby provide electronic shielding.

A flexible front cover 144 is disposed in contact with the metalized layer 106 of bottom portion 112 of foil 102. Front cover 144 may be, for example, silicone rubber. Front cover 144 and the internal components of transducer 100 are fixedly secured by encapsulation 146. Encapsulation 146 may be, for example, a stiff material such as epoxy. A hole 148 throught encapsulation 146, back cover 138, and foil 102 allows the internal air pressure to equalize with the ambient air pressure.

In operation, transducer 100 is held in place over the brachial artery of a patient using, for example, an occlusive cuff with an appropriate fitting (not shown). Front cover 144 of the transducer is placed in contact with the patient's skin. The occlusive cuff is inflated to a pressure above the systolic pressure. As the pressure is slowly released, transducer 100 produces an output signal corresponding to the intra-arterial blood pressure.

In accordance with the invention, the bottom portion 112 of electret foil 102 is adapted to collapse under applied pressures in a range useful for blood pressure measurements. In the collapsed state, the non-metalized layer 104 of foil 102 is in contact with the valleys 124, 126 and 128 between the ridges of back electrode 116.

Figure 3:
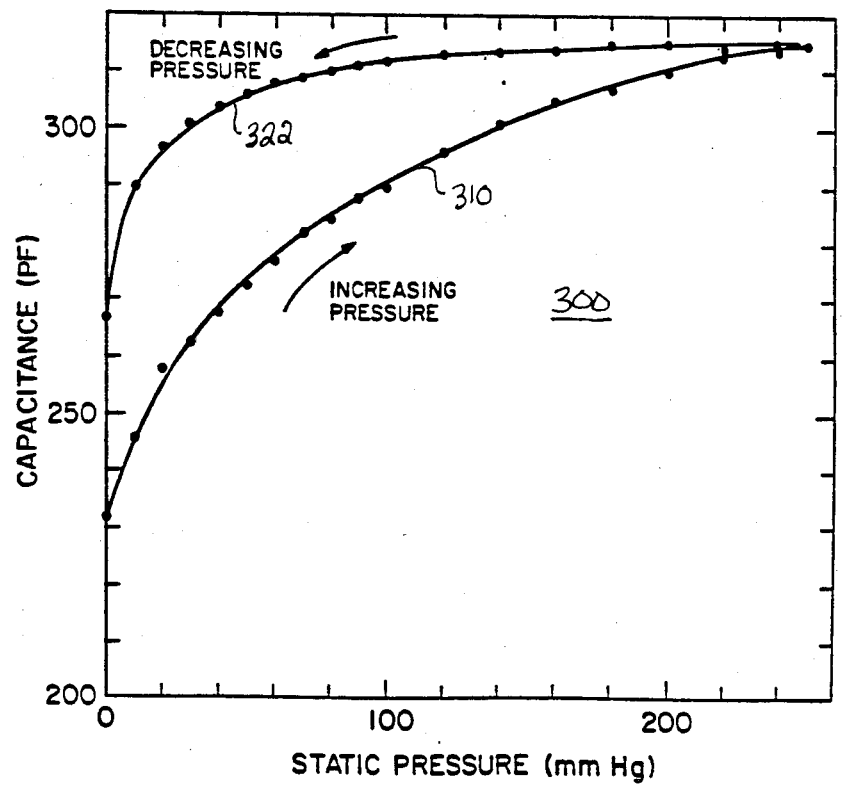
FIG. 3 is a graph showing the capacitance of a transducer in accordance with the invention as a function of static loading pressure.

FIG. 3 is a graph 300 showing the measured capacitance, on the y-axis, of transducer 100 as a function of static pressure, on the x-axis. The measurements were obtained experimentally by placing transducer 100 on an arm and wrapping the arm and transducer with an occlusive cuff having a pressure indicator calibrated in millimeters of mercury (mm Hg). As the cuff static pressure is increased, the bottom portion 112 of foil 102 begins to deflect between ridges 118, 120 and 122 toward back electrode 116. As shown by line 310 in graph 300, the transducer capacitance increases as foil 102 approaches back electrode 116 responsive to increasing pressure. At a pressure of about 20 mm Hg, foil 102 begins to contact electrode 116. At about 250 mm Hg, the foil is considered fully collapsed, as indicated by the flattening of line 310. The static pressure in the cuff is then decreased slowly to obtain Korotkoff signal measurements from the output of transducer 100. It will be noted, as shown by line 320 in graph 300, that the transducer capacitance remains fairly constant as the static pressure is reduced, indicating that the transducer remains in a collapsed state. Not until the pressure is decreased below about 40 mm Hg does the capacitance begin to fall off rapidly. This property is important because the capacitance is directly correlated to the sensitivity (output voltage per unit dynamic pressure) of the transducer. Advantageously, a transducer according to the invention achieves a uniform sensitivity over pressure ranges used for blood pressure readings.

The desirable sensitivity characteristic corresponding to line 320 in graph 300 is achieved according to the invention by establishing the restoring force on foil 102 to be: (a) less than the electrostatic force of attraction between foil 102 and electrode 116 plus the minimum useful static force applied by the cuff during blood pressure readings; and (b) greater than the electrostatic force for attraction alone. The restoring force may be set, for example, by adjusting in combination the density and thickness of the front cover, the thickness and charge density of the electret foil, the spacing between the ridges and the height of the ridges. The mechanics of electret microphones in accordance with the invention are described in greater detail in the article by J. E. West et al. entitled "Foil Electret Transducer for Blood Pressure Monitoring," *J. Acoust. Soc. Am.*, 74(3), (September 1983), pp. 680-686, incorporated by reference herein.

In particular, it has been determined experimentally that foil 102 may have a thickness of about 50 μm, that the spacing between each of the ridges 118, 120 and 122 may be about 4 mm and that the height of ridges 118, 120 and 122 above valleys 124, 126 and 128 may be about 35 μm. A transducer structure is thereby achieved in which the electret foil will collapse and remain collapsed throughout the blood pressure measurement range. In contrast, conventional transducers with ridged backplates are adapted to prevent collapse of the diaphragms throughout their operating range.

While the invention has been described with reference to a preferred embodiment, various modifications and changes may be made by one skilled in the art without departing from the spirit and scope of the invention. For example, the thickness and charge density of the foil, and the spacing and height of the ridges may be changed to provide different operating pressure ranges.

What is claimed is:

1. A pressure transducer comprising:
   a back electrode having two sides with spaced ridges on one side thereof and valley portions disposed between said ridges on said one side; and
   an electret foil having a metalized surface and a charged non-metalized surface; said charged non-metalized surface facing said ridged side of the back electrode and spaced from said back electrode valley portions by said ridges;
   the electret foil being responsive to the pressure applied thereto increasing above a first predetermined value to deflect the foil into contacts with the valley portions of said back electrode, and
   the spacing between the ridges being dimensioned to deflect the foil out of contact with said back electrode valley portions responsive to reducing said pressure below a second predetermined value.

2. A pressure transducer comprising:
   a back electrode having three circular and concentric spaced ridges on one surface thereof;
   an electret foil spaced from the ridged surface of the back electrode having a emtalized surface to which pressure is applied and a charged non-metalized surface facing the ridges surface of the back electrode; characterized in that
   the charged non-metalized electret surface is in a first position in the absence of pressure applied to the metalized surface to maintain a gap between the surface of the back electrode between said ridges and the non-metalized electret surface, and
   the electret foil is responsive to at least a first predetermined pressure applied to the electret metalized surface to deflect to a second position at which the non-metalized surface contacts the back electrode surface between the ridges;
   the ridges being spaced on the back electrode to restore the foil to its first position responsive to reducing the pressure applied to the metalized surface below a second predetermined pressure.

3. Apparatus as in claim 2 wherein
   the ridges have a height of about 35 microns,
   the distance between the ridges is about 4 millimeters, and
   the thickness of the electret foil is about 50 microns.

4. A pressure transducer according to claim 1 wherein said back electrode is conductive.

5. A pressure transducer according to claim 1 further comprising a cover layer disposed in contact with the metalized layer of the electret foil for applying pressure to said electret foil.

6. A pressure transducer according to claim 5 wherein said cover layer is a flexible layer.

7. A pressure transducer according to claim 6 wherein said flexible cover layer is a silicone rubber cover layer.

8. A pressure transducer comprising:
   a back electrode comprising a non-conductive material having spaced ridges on one surface thereof and having the surface portions between the ridges coated with a conductive material;
   an electret foil spaced from the ridges surface of the back electrode having a metalized surface to which pressure is applied and a charged non-metalized surface facing the ridged surface of the back electrode; characterized in that the charged non-metalized electret surface is in a first position in the absence of pressure applied to the metalized surface to maintain a gap between the surface of the back electrode between the ridges and the non-metalized electret surface; and the electret foil is responsive to at least a first predetermined pressure applied to the electret metalized surface to deflect to a second position at which the non-metalized surface contacts the back electrode surface between the ridges;

the ridges being spaced on the back electrode to restore the foil to its first position responsive to reducing the pressure applied to the metalized surface below a second predetermined pressure.

9. A pressure transducer comprising:

a back electrode having spaced ridges on one surface thereof and comprising a back cavity including at least one aperture coupling the back cavity to the gap between the non-metalized surface of the electret and the ridged surface of the back electrode;

an electret foil spaced from the ridged surface of the back electrode having a metalized surface to which pressure is applied and a charged non-metalized surface facing the ridged surface of the back electrode; characterized in that the charged non-metalized electret surface is in a first position in the absence of pressure applied to the metalized surface to maintain a gap between the surface of the back electrode between the ridges and the non-metalized electret surface, and the electret foil is responsive to at least a first predetermined pressure applied to the electret metalized surface to deflect to a second position at which the non-metalized surface contacts the back electrode surface between the ridges, the ridges being spaced on the back electrode to restore the foil to its first position responsive to reducing the pressure applied to the metalized surface below a second predetermined pressure.

10. A pressure transducer comprising:

a back electrode having spaced ridges on one surface thereof;

an electret foil spaced from the ridged surfaces of the back electrode having a metalized surface to which pressure is applied and a charged non-metalized surface facing the ridged surface of the back electrode; characterized in that the charged non-metalized electret surface comprises a Kapton-FEP laminate and is in a first position in the absence of pressure applied to the metalized surface to maintain a gap between the surface of the back electrode between the ridges and teh non-metalized electret surface, and the electret foil is responsive to at least a first predetermined pressure applied to the electret metalized surface to deflect to a second position at which the non-metalized surface contacts the back electrode surface between the ridges;

the ridges being spaced on the back electrode to restore the foil to its first position responsive to reducing the pressure applied to the metalized surface below a second predetermined pressure.

11. A pressure transducer comprising:

a back electrode having spaced ridges on one surface thereof;

an electret foil spaced from the ridged surface of the back electrode having a metalized surface to which pressure is applied and a charged non-metalized surface facing the ridged surface of the back electrode; characterized in that the charged non-metalized electret surface has a charge density of about $10^{-8}$ C/cm$^2$ and is in a first position in the absence of pressure applied to the metalized surface to maintain a gap between the surface of the back electrode between the ridges and the non-metalized electret surface, and the electret foil is responsive to at least a first predetermined pressure applied to the electret metalized surface to deflect to a second position at which the non-metalized surface contacts the back electrode surface between the ridges;

the ridges being spaced on the back electrode to restore the foil to its first position responsive to reducing the pressure applied to the metalized surface below a second predetermind pressure.

* * * * *